United States Patent [19]

Bondar et al.

[11] Patent Number: 4,495,201

[45] Date of Patent: Jan. 22, 1985

[54] PHARMACEUTICAL COMPOSITION AND METHOD FOR TREATING HEART DISEASES THEREWITH

[75] Inventors: Ljudmila S. Bondar; Rostan A. Okunev; Lev V. Polezhaev; Sergei P. Kolchin; Ljudmila V. Cherkasova; Lilia F. Nikolaeva, all of Moscow, U.S.S.R.

[73] Assignees: Institut Organicheskoi Khimii Imeni N.D. Zelinskogo; Vsesojuzny Kardiolgichesky Anuchny Tsentr; Institut Fiologii Razvitia Imeni N.K. Koltsova Akademii Nauk SSSR, all of Moscow, U.S.S.R.

[21] Appl. No.: 382,194

[22] Filed: May 26, 1982

[51] Int. Cl.[3] .......... A61K 31/195

[52] U.S. Cl. .......... 514/560; 514/561

[58] Field of Search .......... 424/319

[56] References Cited

U.S. PATENT DOCUMENTS

| | | | |
|---|---|---|---|
| 3,840,571 | 10/1974 | Bondar et al. | 562/571 |
| 3,991,086 | 11/1976 | Bondar et al. | 562/553 |

*Primary Examiner*—Albert T. Meyers

*Assistant Examiner*—John W. Rollins

*Attorney, Agent, or Firm*—Burgess, Ryan and Wayne

[57] ABSTRACT

A novel pharmaceutical composition for treating heart diseases according to the present invention comprises -4′,5,9-trimethyl-2-(4′-aza-amyl)-decadi-4,8-ene acid of the formula:

$$CH_3-\underset{}{\overset{CH_3}{\overset{|}{C}}}=CH-CH_2-CH_2-\overset{CH_3}{\overset{|}{C}}=CH-CH_2-\overset{COOH}{\overset{|}{C}H}-CH_2-CH_2-CH_2-\overset{CH_3}{\overset{|}{N}}-CH_3$$

and a pharmaceutical carrier.

A method of treating heart diseases using the present composition is also disclosed.

6 Claims, No Drawings

PHARMACEUTICAL COMPOSITION AND METHOD FOR TREATING HEART DISEASES THEREWITH

FIELD OF APPLICATION

The present invention relates to medicine and, more specifically, to a novel pharmaceutical composition for treating heart diseases. The composition according to the present invention is useful in medicine for treating myocardial infarction, myocarditis, myocardiopathy, and myocardial distrophy.

DESCRIPTION OF THE PRIOR ART

Various preparations useful in the treatment of myocardium are known in the art. Such preparations include Inosine-F comprising a nucleoside-hypoxanthine riboside, orotic acid (2,6-dihydroxypyrimidine-4-carboxylic acid), its potassium and other salts, vitamin $B_{12}$ with folic acid, anabolic hormones such as retabolyl (nandrolone decanoate $C_{28}H_{44}O_3$) and the like. All the above-listed preparations, while acting on myocardial metabolism, do not provide any direct effect on the zone of the cardiac muscle necrosis. Furthermore, the above-mentioned prior art preparations manifest no clear-cut effect on the rate of formation of a post-infarction scar and fail to prevent the development of post-infarction heart aneurysm.

SUMMARY OF THE INVENTION

The present invention is directed to a novel pharmaceutical composition which provides a stimulant effect on processes of the formation of a post-infarction scar and a correcting effect on the state of the peri-infarction zone, as well as preventing the development of insufficiency of blood circulation and post-infarctional heart aneurysm. The composition exhibits a low toxicity, a wide range of therapeutical action and a reduced duration of treatment.

The compound used as the active ingredient according to the present invention is disclosed in U.S. Pat. Nos. 3,840,571 and 3,991,086. According to the present invention, the composition for the treatment of cardiac muscle diseases comprises the compound-4',5,9-trimethyl-2-(4'-aza-pentyl)decadi-4,8-ene acid of the following general formula:

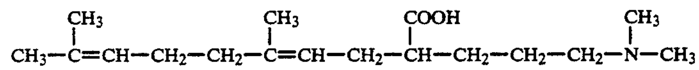

and a pharmaceutical carrier.

The composition according to the present invention can be used in different forms. It is preferred to administer the medicated composition according to the present invention as injection solutions, tablets and suppositoria.

The composition in the form of injection solutions preferably contains the compound in the amount of from 1.5 to 5% by weight. The carrier can be bidistilled water, an aqueous solution of sodium chloride, Ringer solution, or a solution of glucose.

The composition in the form of tablets or suppositoria preferably contains the compound in an amount of from 0.025 to 0.05 g per tablet or suppository. For suppositoria use can be made of any pharmaceutically suitable base; for tablets as the pharmaceutical carrier use can be made of preferably starch, lactose, glucose. The composition according to the present invention provides a stimulant effect on the rate of formation of a post-infarctional scar without affecting normal heart functioning, and with accelerated, positive dynamics of electrocardiogram, a lesser frequency of the formation of a post-infarctional heart aneurysm. Furthermore, there is a lesser frequency of blood-circulation insufficiency especially in patients with transmural and vast myocardial infarctions. Finally there is a clearly pronounced chronotropic effect and a positive inotropic effect as well.

Under the action of the preparation according to the present invention there are intensified: lysis of the necrotized tissue, substitution of the necrosis zones with connective tissue and collagenation thereof. At the same time, resorption of necrotic masses is considerably accelerated with simultaneous rapid filling of the infarcted region with cellular elements of the connective tissue and accelerated formation, in this region, of a dense-elastic scar. Physiological effects of the composition according to the present invention are due to accelerated formation of the post-infarction scar, thus improving conditions for functioning of the heart muscle on the whole and intensifying oxidation processes in the perinecrotic zone and (during the initial stage of the disease) in the extra-infarctional areas of myocardium. It should be noted that these effects are not accompanied by an increased rate of oxygen consumption by the heart.

The composition according to the present invention improves the contractile function of myocardium, as well as parameters of the central hemodynamics in the case of diphtheric myocarditic.

Intensification of protein synthesis in myocardium is also noted under the action of the preparation according to the present invention. The composition of the invention possesses a clearly pronounced cholinomimetic and adrenolytic effect and has a marked influence on the activity of pacemaking structures of the heart. The composition of the present invention has low toxicity, small single and course doses, a wide range of theraupetic action and a short duration of the treatment course. The preparation is useful for treating heart diseases, myocardial infarction in particular. The administration of the composition is especially indicated in patients with the most severe forms of myocardial infarction—vast and transmural myocardial infarctions and also in patients with myocarial infarctions against the background of a high arterial pressure menacing by the formation of a post-infarctional heart aneurysm. Furthermore, the composition according to the present invention is useful in the treatment of myocarditises aggravating the course of infectional diseases, myocardipathies, myocarcardiodistrophiae, and also after surgical interventions of the heart, accompanied by dissection of myocardium and for prevention of the subsequent complications: cardial insufficiency after myocardial infarction and myocarditises, and formation of post-infarctional heart aneurysms.

DETAILED DESCRIPTION OF THE INVENTION

The composition according to the present invention has been experimentally tested on animals and in clinics on patients.

The experiment on animals has been performed on 419 rabbits of the Chinchilla variety with experimentally-induced myocardial infarction produced by ligation of the front descending branch of the coronary artery.

The effect of the composition according to the present invention on the progress of the experimental myocardial infarction has been studied in comparison with the effect produced by inosine, potassium orotate, vitamin $B_{12}$ with folic acid and retabolyl.

Histological, histochemical and electron-microscopic methods of investigation have been employed to study the zone of necrosis, perinecrotic zone and myocardium regions spaced from the place of infarction by 1, 3 and 7 days after operation. Furthermore, to determine the contractile ability of myocardium, measurements of intracavitary pressure have been performed. Dynamic electrocardiographic observation over the animals was carried out 7 times during the first day (prior to operation, 15, 30 minutes, 1, 2, 3 and 4 hours after the administration) and during the following days two times a day (before and one hour after the administration).

The study of the total cross-sectional patterns of a rabbit's heart has made it possible to precisely define these zones.

The first group of rabbits has been intramuscularly injected with the composition according to the present invention in the dose of 1 mg/kg in a day.

The second group of rabbits has been injected with inosine in a dose of 30 mg/kg intravenously daily once a day; for the first time 16 hours after the operation and for the last time 2 hours before slaughter (i.e. before the 7th day). The third group of rabbits has been given potassium orotate in a dose of 30 mg/kg in the same sequence as the previous preparation, i.e. up to the 7th day.

The fourth group of animals has been administered vitamin $B_{12}$ 3γ/kg in combination with folic acid in the same sequence.

The fifth group of rabbits has been administered an anabilic hormone of a prolonged action—retabolyl in a dose of 5 mg/kg of the bodyweight 1-2 times intramuscularly up to the 7th day.

As a result of the studies it has been found that the composition according to the present invention exerts the most pronounced effect on reparative processes in the zone of necrosis. Administration of the preparation of the invention accelerates processes of resorption of necrotic masses and replacement thereof with connecting tissues. The rate of the processes of maturation of connective-tissue fibres, and collagenation thereof are increased. The acceleration of resorption of necrotic masses occurs both at the account of intensification of infiltration of the necrosis zone with cellular elements represented mainly by macrophages, and, to a greater extent, owing to a greater activation of enzymes of esterase, aminopeptidase acid and alkali phosphatases, ensuring lysis of necrotic masses in perinecrotic areas and retained cellular elements of the necrosis zone.

A considerable role in energetic and plastic sources for the processes of reparation stimulated by the composition according to the present invention is taken by an increased activity, under these conditions, of reactions of a pentose-phosphate shunt which can be judged upon by increasing activity of glucoso-6-phosphatehydrogenase in perinecrotic areas of myocardium and in cellular elements of the zone of necrosis.

Of a certain importance are changes of microcirculatory channel in perinecrotic areas of myocardium revealed by electron microscopy. A greater, as compared to the control, manifestation of the phenomenon of micropinocytosis in cytoplasm of endothelium of capillaries and an increased number of microvilli, while demonstrating an increased permeability of the walls of vessels, serve to facilitate the processes of resorption of necrotized masses.

The effect of inosine on the process of the formation of a post-infarction scar also takes place, but it is substantially less pronounced than the effect of the preparation according to the present invention due to some other mechanisms. While upon administration of the composition according to the present invention resorption of necrotic masses is effected through an enhanced infiltration of the zone of necrosis with cellular elements and owing to increased activity of enzymes ensuring lysis in the zone of necrosis and perinecrotic areas of myocardium, upon administration of inosine the main part in these processes is taken by enhanced cellular infiltration of the zone of infarction, whereas increasing activity of lysis-ensuring enzymes is limited only to the zone of necrosis.

Potassium orotate and vitamin $B_{12}$ with folic acid provides still less pronounced effect on processes of organization of the post-infarction scar slightly increasing activity of "lysing" enzymes in the zone of necrosis and some reactions of pentose-phosphate shunt in perinecrotic areas of myocardium.

The effect of retabolyl on reparative processes in the zone of necrosis is less pronounced.

In the study of the effect of the composition according to the present invention on metabolic processes in extra-infarction areas of myocardium there has been noticed an increased activity of lactatedehydrogenase which contributes to minimization of the phenomena of acidosis with a possible improvement, owing thereto, of conditions of functioning of contractile mechanisms. A similar effect has been obtained, in this respect, from the use of inosine; slightly less pronounced effect is characteristic for potassium orotate, vitamin $B_{12}$ with folic acid and retabolyl.

The analysis of electrocardiographic data has revealed a clear-cut effect of the composition according to the present invention on the dynamics of the terminal part of the ventricular complex.

In the control group of animals and in the group treated with the composition according to the present invention after reproduction of an experimental myocardial infarction in the branch $V_s$ has been recorded either complex QS with a lifted segment ST in the form of a single-phase curve at the transmural infarction, or a high arc-like wave T with the preserved wave R. Later in the group of animals administered with the composition according to the present invention there has been noted a considerable acceleration of normalization of the terminal part of the ventricular complex. Thus, while in the control the formation of the negative phase of wave T is noted by the 4th-5th of the experimental myocardial infarction, in the main group it is observed already 3-4 hours after operation. Decrease of the range ST to isoline in the control occurs by the 2nd-4th day, whereas in the experiment—within 12-24 hours. None of the simultaneously studied preparations has shown similar effect on the dynamics of the ventricular complex. It should be noted that in some cases of transmural myocardial infarction there is observed the appearance of a previously lacking wave R due to the use of the composition according to the present invention, while in the control this wave R is not recorded. The degree of increasing of voltage of the complex QRS in the group of animals administered with the composition of the present invention is also pronounced more distinctly than in the control, though to a lesser extent that in the case of inosine.

In the study of toxic doses (8 mg/kg) of the composition according to the present invention on the dynamics of ECG, 10 minutes after the intravenous injection thereof it has been noted a trough-shaped reduction of the range ST retained over 32–48 hours; in 8 out of 20 rabbits there is observed a delayed atrioventricular conduction 1–2 hours after injection. No such phenomenon has been observed upon administration of therapeutic doses.

In the study of intracardiac hemodynamics under the effect of the composition according to the present invention there has been noted an increase in the speed of growth and the speed of drop of pressure in the left ventricle of the heart. The effect of the composition according to the present invention on characteristics of intracardiac hemodynamics is less pronounced than that of inosine or potassium orotate due to a more marked effect of the latter agents on processes of the formation of a compensatory hyperfunction and hypertrophy of extrainfarction areas of the heart muscle.

The effect of the composition according to the present invention has been studied in experimental diphtheric myocarditis in rabbits. The composition according to the present invention accelerates the process of rehabilitation of deteriorated functions of the heart and healing of the injury spots. Under the action of the composition of the present invention in rabbits with myocarditis there is observed normalization of ECG, increased force of cardiac contractions and tolerance of the heart to higher loads is increased.

The composition according to the present invention has low-toxicity. The tolerated dose of the preparation on white mice in the case of intraperitoneal administration is 0.01 g/kg, upon hypodermal administration—0.05 g/kg, upon intramuscular administration—0.05 g/kg. A mean lethal dose ($LD_{50}$) on white mice upon intraperitoneal administration is 0.06 g/kg hypodermal administration—0.4 g/kg, intramuscular administration—0.16 g/kg. The toxic dose causing noticeable changes in ECG of rabbits upon intravenous injection is 2 mg/kg. In histological studies of lungs, liver and kidney of guinea pigs administered with the composition according to the present invention in a dose of 200 mg (0.9 g/kg of the bodyweight) singly and daily over 5 days no pathological changes have been observed. In the study of the heart and liver of the test animals administered with the composition according to the present invention no signs of malignant growth have been observed. Upon incubation of embryos of loach following the commonly accepted procedure with different concentrations of the composition according to the invention from 1:2500 to 1:250,000 (400 μg/ml to 4 μg/ml), no deviations from normal development of the embryos and their hatching were observed. The toxic effect of the composition according to the present invention revealed in the concentration of 1:10,000 (100 μg/ml) and above is reflected in death of a portion of the embryos.

The composition according to the present invention has been tested in clinical conditions on 536 patients suffering from myocardial infarction including a control group consisting of 162 persons (i.e. patients treated by composition commonly adopted in the modern medical practice).

The composition according to the present invention is administered to the patients intramuscularly in a dose of from 25 to 50 mg once every three days. The treatment course covers 3–5 injections; the course dose is 75 to 125 mg.

Prior to studying the effect ensured by the composition according to the invention on patients, the preparation has been tested on 2 healthy men.

The control over the effect of the comparison in the patients has been effected by means of a monitoring system of observation over ECG during the first 3–4 days of the illness (the first three days—daily). A further dynamic electrocardiographic observation is effected during the first day of injection of the composition (prior to injection and 1 and 2 hours thereafter), then once per 3 and later on—per 5 days. On the 1th, 10th, 20th and 40th days of the disease the central hemodynamics was determined by the method of radiocardiography. On the 10th and 40th days of the illness the contractile capacity of myocardium is assessed by methods of electro- and X-ray kymography. The biochemical control over the effect of the preparation was effected by determination, in dynamics in blood serum, of the products of decomposition of DNA, proline, hydroxyproline, transaminases. There was also analyzed the dynamics of normalization of leukocytosis, ESR (erythrocyte sedimentation rate), disappearance of aneosinophilia. The careful clinical assessment of the effect of the composition was also performed.

First of all, there was established a prolonged effect of the composition according to the present invention. Its effect is still revealed after 16–22 hours from the moment of intramuscular injection and retained for 48–72 hours. This enabled a conclusion on the expediency of injection of inosine of once per every 3 days. The analysis of the dynamics of ECG demonstrates acceleration of the reduced range ST and the formation of a deep negative coronary wave T (on the 7th–10th day in the main group of patients as compared to the 14th–18th day in the control group). Furthermore it was noted that the voltage of wave R reduced in the acute stage was growing at an accelerated rate.

In some cases there was noted a chronotropic effect of the composition according to the present invention—the frequency of cardiac contractions during the treatment course was less by 12–18 contractions per minute, while increasing to a certain extent on completion of administration of the composition.

Accelerated normalization of the content, in blood serum, of decomposition products of DNA, proline and hydroxyproline demonstrates acceleration of maturation of connective-tissue elements in the region of the post-infarction scar, thus complementing the data of the dynamic electrocardiographic observation.

The analysis of the data of radiocardiography has revealed some acceleration of positive shift towards normalization in respect of cardiac and systolic indices in patients administered with the composition of the present invention.

On the 20th day of the illness the cardiac index in the control group was 2.32±0.08 l/min/m$^2$, the basic—2.38±0.04 l /min/m$^2$, systolic index—24.8±0.21 ml/m and 27.8±0.51 ml/m respectively. On the 40th day of the illness the cardiac index in the patients of the control group was 2.55±0.01 l/min/m$^2$, in the basic group—2.62±0.04 l/min/m$^2$, the systolic index was 29.8±0.24 and 33.1±0.31 ml/m, respectively.

The study of clinical data leads to the conclusion that there is less frequency of the signs of insufficiency of blood circulation upon administration of the composition according to the present invention. This effect of the composition as compared to the control group of patients is more clearly pronounced in a more distant period of the disease upon a substantial enlargement of the patient's conditions (insufficiency of blood circulation on the 20th–40th day of the illness was revealed in 10.4% of patients of the control group and 21.0% of the patients of the control group).

Analysis of the data of X-ray and electrokymography has indicated decrease in the number of cases of the development of aneurysm in the test group of patients as compared to the control.

In the study of the central hemodynamics by the method of radiocardiography with the introduction of human albumin labelled with $I^{131}$ in the patients administered with the composition according to the present invention and inosine it has been noticed, as compared to the control, a more pronounced and earlier regaining of such hemodynamic characteristics as cardiac and systolic indices, beat work of the heart and the like. In the comparative analysis of the effect of the composition according to the present invention and inosine on the state of blood circulation in patients suffering from myocardial infarction the following has been found. The composition according to the present invention having its effect directed mainly to processes of the formation of a post-infarction scar and the state of the periinfarction zone has proven to be most efficient in respect of insufficiency of blood circulation in patients with a vast and transmural myocardial infarction, i.e. in those patients which have blood circulation insufficiency mainly due to a specific role played by exclusion of a wide zone of necrosis from the contractile act. Inosine, having its effect directed mainly to extra-infarction areas of myocardium, exerts the most pronounced effect on the state of blood circulation in patients with a repeated myocardial infarction, accompanying hypertonic disease, in aged persons having insufficiency of blood circulation after myocardial infarction due to an essential part taken not only by the formation of a zone of necrosis, but disturbance of metabolic processes, functional properties of the heart muscle on the whole which has taken place in the pre-infarction period because of post-infarction cardiosclerosis, diffusive cardiosclerosis in old people, metabolic changes due to a long-term hyperfunction of myocardium in patients suffering from hypertonia. The analysis of electrocardiographic changes in patients administered with the composition according to the present invention the following phenomena have been observed: in addition to acceleration of normalization of voltage of the wave R and wave P, the reduction of the range ST till the isoline is accelerated to 7.2 days as compared with 14.2 days on the average in the control. The formation of the negative coronary wave T occurs by the 6th–8th day of the disease as compared to 11.2 days on the average in the main group.

These data correspond to acceleration of normalization of the content, in blood, of acid-soluble products of decomposition of DNA on the 7th day of the disease on the average in the case of the composition according to the present invention and on the 10th day of the illness in the case of inosine as compared to the 15th day in the control group and acceleration of reduction of the content of hydroxyproline in blood, reflecting, as it is well known, the metabolism of collagen (by the 20th day instead of the 40th day in the control).

Taking into consideration the impossibility of identifying of patients of the control and main groups, with the view to obtain objective data, the method of mathematical forecasting has been employed. It has made it possible to forecast the expected outcome and complications of the disease starting from particularities of the clinical pattern of the disease in the acute period (49 features altogether) and compare them with those which have taken place in reality. The data of the mathematical forecasting have proven the efficiency of the composition according to the present invention in respect of prophylaxis of the development of insufficiency of blood circulation and post-infarctional aneurysm. Postinfarction aneurysm and insufficiency of blood circulation have been revealed in a lesser number of cases than it had been forecast. In all cases of administration of the composition of the present invention a good toleration thereto has been noted. The administration of the composition according to the present invention in therapeutic doses does not change the intraventricular conduction, neither does it cause signs of blockade. The composition according to the present invention has no influence on the value of arterial pressure. In some cases at a low arterial pressure there is noted a moderate elevation thereof to normal parameters.

Therefore, on the basis of the tests thus performed the following conclusion has been made. The composition according to the present invention is very effective, having a selective action on the heart. It increases the force of cardiac contractions, rarefies rhythm of a healthy heart and has an influence on the dynamics of electrocardiographic signs reflecting the formation of a post-infarctional scar, and accelerates healing of the heart muscle. It also intensifies lysis of the necrotized tissue, replacement of necrosis zones with a connective tissue and collagenation thereof. The resorption of necrotic masses is considerably accelerated simultaneously with a rapid filling of the infarcted region with cellular elements of a connective tissue and acceleration of the formation of a dense-elastic cicatrix at this point. Under the effect of the composition according to the present invention the positive dynamics of pathological electrocardiographic shifts, characteristics of functional states of myocardium and the central hemodynamics in myocardial infarction is accelerated. In patients suffering from myocardial infarction the composition of the present invention improves the contractile function of the heart muscle and serves as an agent preventing the formation of a post-infarctional heart aneurysm.

The preparation also improves the contractile function of myocardium and characteristics of the central hemodynamics in the case of diphtherial myocarditis.

Physiological effects of the composition according to the present invention are due to acceleration of the formation of a post-infarctional scar which improves the conditions for functioning of the heart muscle on the whole, as well as increases activity of oxidation processes in the perinecrotic zone and (in the initial period of the disease) in extra-infarction areas of myocardium so that it is not accompanied by an increased consumption of oxygen by the heart. The composition according to the present invention provides no negative effects on the level of arterial pressure; it has a low toxicity and a longer duration of its action amounting to a period of from 48 to 72 hours.

The composition according to the present invention can be administered in different pharmaceutical forms. (injection solutions, tablets, suppositoria and the like).

According to the present invention, it is preferable to use the composition in the form of injection solutions, tablets and suppositoria. The invention also resides in a method of treating heart diseases, according to which the preparation is introduced either in the form of injection solutions or intramuscularly in a dose of 0.05 to 0.075 g once a day every other day during a period of 5 to 9 days. In the case of use of the composition as injections, it is administered intramuscularly in the dose of 0.05 g (1 ml of a 5% solution) once a day every other day in the amount of 3–5 injections starting from the third day of the disease, i.e. on the 3, 5, 7, 9 and 11th day of the disease. The average daily dose upon administration every other day is 0.028 g (0.56 ml of a 5% solution, 28 mg), the course dose is 0.15 to 0.25 g (3–5 ampules by 3–5.0 ml, 150–250 mg).

The maximum single dose is 0.10 g; the maximum average daily dose is 0.056 g; the maximum course dose is 0.3–0.5 g. The duration of the course of treatment with the composition according to the present invention is 5 to 9 days. In the case of administration of tablets, the composition of the present invention is administered in a dose of 0.025 g and 0.05 g—1 tablet once a day every other day. The treatment course is 5 to 9 days. Suppositoria are administered by 0.05 and 0.025 g as 1–2 suppositoria daily every other day. The treatment course lasts for 5 to 9 days.

The treatment by the composition according to the present invention is carried out under obligatory daily electrocardiographic control. Special attention should be paid to atrio-ventricular and intraventricular conduction because negative changes thereof points to an overdosage of the composition. Treatment with the composition according to the present invention usually is well tolerated by patients. In individual patients the administration of the maximum dose of the composition can be accompanied with disturbances of atrio-ventricular or intraventricular conduction. In the case of appearance of signs of blockade, the administration of the composition should be stopped (the blockade phenomena disappear without any special treatment upon discontinuation of administration of the preparation).

The lowering of the range ST in an electrocardiogram below the isoline is not a complication and cannot be regarded as the ground for discontinuation of the treatment course using the composition according to the present invention or cancellation thereof.

Contraindications to administration of the composition according to the present invention are the presence of an atrio-ventricular or intraventricular blockade and liability to bradycardia.

The composition according to the present invention is prepared by conventional methods. The compound which is the active ingredient-4', 5,9-trimethyl-2-(4'-azapentyl)-decadiene-4,8 acid is obtained by a known method consisting in the following. Malonic ester is twice alkylated with geranylhalide and dimethylaminopropylchloride in the presence of a strong base or in a reverse sequence with isolation of intermediate mono- and di-substituted malonic esters, followed by saponification of dimethylaminopropylgeranylmalonic ester, isolation of di-substituted malonic acid, its thermal decarboxylation and purification by vacuum-distillation to give the desired product.

4',5,9-trimethyl-2-(4'-aza-pentyl)-decadi-4,8-ene acid is a transparent very viscous light-yellow liquid with a greenish shade to reddish-yellow with brownish shade colour with characteristic odour of amines and slightly bitter taste. It is well soluble in water, aqueous solutions of strong acids, alkalis, in diluted solutions of salts, in the majority of organic solvents (ethanol, ether, acetone, gasoline, benzene), as well as in fats and vegetable oils. Aqueous solutions of the compound are transparent, stable and can be sterilized by conventional methods. The compound according to the present invention is classified in List A, stable in storage and should be stored at a temperature of not more than 25° C. The advisable period of storage is two years.

We claim:

1. A pharmaceutical composition for treating heart diseases selected from the group consisting of myocardial infarction, myocarditis, myocardiopathy, and myocardial dystrophy comprising an injectable solution containing from 1.5 to 5% by weight of the compound 4',5,9-trimethyl-2-(4'-azapentyl)-decadi-4,8-ene acid of the following formula:

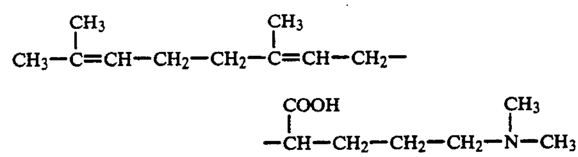

in combination with a pharmaceutically acceptable carrier.

2. The composition according to claim 1, wherein said carrier is bidistilled water, an aqueous solution of sodium chloride, Ringer's solution, or a solution of glucose.

3. A pharmaceutical composition for treating heart diseases selected from the group consisting of myocardial infarction, myocarditis, myocardiopathy and myocardial dystrophy in the form of a tablet or a suppository containing between 0.025 and 0.05 g. of the compound 4',5,9-trimethyl-2-(4'-azapently)-decadi-4,8-ene acid of the following formula:

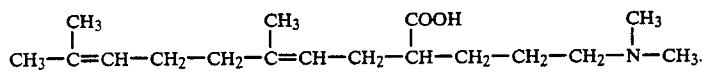

4. A method of treating heart diseases selected from the group consisting of myocardial infarction, myocarditis, myocardiopathy, and myocardial dystrophy in a warm-blooded animal comprising administering to said warm-blooded animal an injectable solution containing from 1.5 to 5% by weight of the compound 4',5,9-trimethyl-2-(4'-azapentyl)-decadi-4,8-ene acid of the following formula:

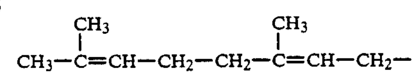

-continued
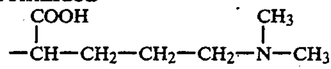
in combination with a pharmaceutically acceptable carrier.
5. The method of claim 4 comprising administering an injectable solution of said compound into said warm blooded animal at a dosage of between 0.05 and 0.075 g. of said compound.
6. The method of claim 5 wherein said injectable solution is administered every other day for between 5 to 9 days.
* * * * *